US005639732A

United States Patent [19]
Mallamo et al.

[11] Patent Number: 5,639,732
[45] Date of Patent: Jun. 17, 1997

[54] PHOSPHOROUS-CONTAINING CYSTEINE AND SERINE PROTEASE INHIBITORS

[75] Inventors: John P. Mallamo, Glenmore; Ron Bihovsky, Wynnewood; Ming Tao, Maple Glen; Gregory J. Wells, West Chester, all of Pa.

[73] Assignee: Cephalon, Inc., West Chester, Pa.

[21] Appl. No.: 679,342

[22] Filed: Jul. 10, 1996

Related U.S. Application Data

[60] Provisional application No. 60/001,491 Jul. 17, 1995.
[51] Int. Cl.[6] .............. A61K 31/66; C07F 9/09; C07F 9/30; C07F 9/32
[52] U.S. Cl. .............. 514/23; 514/110; 514/119; 536/18.7; 544/157; 548/413; 558/73; 558/82; 558/83; 558/86; 558/170; 558/174; 562/15
[58] Field of Search .................... 514/110, 119, 514/23; 544/157; 548/413; 558/73, 170

[56] References Cited

FOREIGN PATENT DOCUMENTS

0644197A1  3/1995  European Pat. Off. .

OTHER PUBLICATIONS

Dolle, R.E. et al., "Aspartyl α-((Diphenylphosphinyl)oxy) methyl Ketones as Novel Inhibitors of Interleukin-1β Converting Enzyme. Utility of the Diphenylphosphinic Acid Leaving Group for the Inhibition of Cysteine Proteases", *J. Med. Chem.*, 1995, 38, 220–222.
Harbeson, Scott L. et al., "Inhibition of Aminopeptidases by Peptides Containing Ketomethylene and Hydroxyethylene Amide Bond Replacements", *J. Med. Chem.*, 1989, 32, 1378–1392.
Repine, Joseph T. et al., "Renin Inhibitors Containing α–Heteroatom Amino Acids as $P_2$ Residues[1]", *J. Med. Chem.*, 1992, 35, 1032–1042.
Rich, Daniel H. et al., "New Hydroxyethylamine HIV Protease Inhibitors That Suppress Viral Replication", *J. Med. Chem.*, 1992, 35, 3803–3812.
Goel, O.P. et al., *Org. Syn.*, 1993, Coll. vol. VIII, 68.
Montchamp, J. et al., "Double Arbuzov Reaction of in Situ Generated Bis(trimethylsiloxy)phosphine with Dielectrophiles: Methodology for the Synthesis of Cyclic Phosphinic Acids", *J. Org. Chem.*, 1995, 60, 6076–6081.
Froestl, W. et al., "Phosphinic Acid Analogues of GABA. 2. Selective, Orally Active $GABA_B$ Antagonists", *J. Med. Chem.*, 1995, 38, 3313–3331.
Adams, R.R. et al., "Heterocyclic Basic Compounds. IV. 2–Aminoalkylamino–pyrimidines[1]", *J. Am. Chem. Soc.*, 1945, 67, 735–738.
Texier–Boullet, F. et al., "A Convenient Synthesis of Dialkyl 1–Hydroxyalkanephosphonates using Potassium or Caesium Fluoride without Solvent", *Synthesis*, 1982, 165.
Schlemmer, H. et al., "Phosphorus–31 Nuclear Magnetic Resonance Spectroscopy of the Phosphorylated Tetrapeptide Gly–Gly–Asp–Ala", *Magn. Reson. Chem.*, 1988, 26(3), 260–3, abstract. (Note compound with registricy no. 117289–76–6.) (Database CAPLUS on STN International, Chemical Abstracts Service, (Columbus, OH), Accession No. 1988:611439.).
Sterling–Winthrop, Inc., "Preparation of Peptide Derivatives as Interleukin 1β–converting Enzyme Inhibitors", JP 07025887 A2, *Jpn. Kokai Tokkyo Koho*, 1995, abstract. (Note listing of disclosed compounds.) (Database CAPLUS on STN, Chemical Abstracts Services, (Columbus, OH), Accession No. 1995:867576.).
Ramage, R. et al., "Application of Phosphinic Acids to Peptide Synthesis", *Pept. Proc. Eur. Pept. Symp.*, 17th, (1983), Meeting Date 1982, 157–62, abstract. (Note compound with registry no. 88577–10–0.) (Database CAPLUS on STN, Chemical Abstracts Services, (Columbus, OH), Accession No. 1984:51966.).

*Primary Examiner*—Johann Richter
*Assistant Examiner*—Michael G. Ambrose
*Attorney, Agent, or Firm*—Woodcock Washburn Kurtz Mackiewicz & Norris LLP

[57] ABSTRACT

The present invention is directed to novel phosphorous-containing inhibitors of cysteine or serine proteases. Methods for the use of the protease inhibitors are also described.

44 Claims, No Drawings

PHOSPHOROUS-CONTAINING CYSTEINE AND SERINE PROTEASE INHIBITORS

CROSS REFERENCE TO RELATED APPLICATIONS

This application claims benefit of U.S. provisional application Ser. No. 60/001,491, filed Jul. 17, 1995.

FIELD OF THE INVENTION

Novel inhibitors of cysteine or serine proteases, referred to herein as β-keto phosphates, β-keto phosphinates, β-keto phosphonates, α-keto phosphonates, α-keto phosphinates, and α-keto phosphine oxides, methods for making these novel compounds, and methods for using the same are disclosed.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Specific β-keto phosphinates have been described as inhibitors of ICE, cathepsin B, and calpain (R. E. Dolle, et al., J. Med. Chem. 1995 38, 220–222). See also European Patent Application Pub. No. 0 644 197 A1.

Cysteine proteases are also produced by various pathogens. The cysteine protease clostripain is produced by *Clostridium histolyticum*. Other proteases are produced by Trpanosoma cruzi, malaria parasites *Plasmodium falciparum* and *P. vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to novel cysteine and serine protease inhibitors referred to herein as β-keto phosphates, β-keto phosphinates, β-keto phosphonates, α-keto phosphonates, α-keto phosphinates, and α-keto phosphine oxides. These novel compounds are represented by the following Formula I:

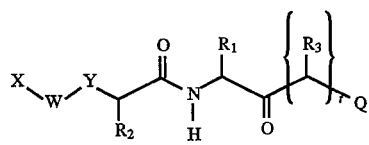

wherein:

X is aryl having from about 6 to about 14 carbons, heteroaryl having from about 6 to about 14 ring atoms, aralkyl having from about 7 to about 15 carbons, alkyl having from 1 to about 10 carbons, said alkyl groups being optionally substituted with one or more J groups, heteroalkyl having from 2 to about 7 carbons, alkoxy having from 1 to about 10 carbons, aralkyloxy having from about 7 to about 15 carbons, or a carbohydrate moiety optionally containing one or more alkylated hydroxyl groups;

W is carbonyl or $SO_2$;

Y is NH or $(CH_2)_k$ where k is an integer from 0 to 3;

$R_1$ and $R_2$ are independently hydrogen, alkyl having from one to about 14 carbons, or cycloalkyl having from 3 to about 10 carbons, said alkyl and cycloalkyl groups being optionally substituted with one or more J groups;

$R_3$ is hydrogen, lower alkyl, aryl, heteroaryl, aralkyl, or heteroaralkyl;

t is 0 or 1;

J is halogen, alkyl, aryl, heteroaryl, amino optionally substituted with one to three aryl or lower alkyl groups, guanidino, alkoxycarbonyl, alkoxy, hydroxy, aryloxy, aralkyloxy, heteroalkyl, or carboxy; and Q has the formula $$-(O)_z-P(=O)(O)_m-R_4)(O)_n-R_5)$$

wherein:

m, n, and z are each independently 0 or 1;

$R_4$ and $R_5$ are each independently hydrogen, lower alkyl optionally substituted with J, aryl optionally substituted with J, aralkyl optionally substituted with J, or heteroaryl optionally substituted with J;

or $R_4$ and $R_5$ may be taken together along with the $-(O)_m-P(=O)-(O)_n-$ of Q to form a 5–8 membered heterocyclic ring, optionally substituted with J;

or $R_4$ and $R_5$ taken together may form an aralkyl group; with the proviso that when t is 0, z is also 0; and with the proviso that when m and n are both 0, and t and z are both 1, $R_4$ and $R_5$ cannot be unsubstituted phenyl or halogen-substituted phenyl; and with the further proviso that $R_1$ cannot be methylene substituted with a carboxyl group.

Some preferred embodiments of the compounds of Formula I are represented by compounds having the Formula Ia:

Ia wherein X, $R_4$, $R_5$, m and n are as previously defined.

The compounds of the invention are useful for the irreversible inhibition of cysteine and serine proteases. Beneficially, these compounds find utility in a variety of settings. For example, in the research arena, the claimed compounds can be used, for example, in discovery of agents for treating disorders associated with abnormal and/or aberrant activity of cysteine and/or serine proteases. In a clinical arena, for example, the compounds can be used to alleviate, mediate, reduce, and/or prevent disorders which are associated with abnormal and/or aberrant activity of cysteine and/or serine proteases. Methodologies for making our β-keto phosphates, β-keto phosphinates, β-keto phosphonates, α-keto phosphonates, α-keto phosphinates, and α-keto phosphine oxides are also disclosed.

These and other features of the compounds of the subject invention are set forth in more detail below.

DETAILED DESCRIPTION

Novel cysteine and serine protease inhibitors have been discovered which are represented by the general Formula I:

I wherein:

X is aryl having from about 6 to about 14 carbons, heteroaryl having from about 6 to about 14 ring atoms, aralkyl having from about 7 to about 15 carbons, alkyl having from 1 to about 10 carbons, said alkyl groups being optionally substituted with one or more J groups, heteroalkyl having from 2 to about 7 carbons, alkoxy having from 1 to about 10 carbons, aralkyloxy having from about 7 to about 15 carbons, or a carbohydrate moiety optionally containing one or more alkylated hydroxyl groups;

W is carbonyl or $SO_2$;

Y is NH or $(CH_2)_k$ where k is an integer from 0 to 3;

$R_1$ and $R_2$ are independently hydrogen, alkyl having from one to about 14 carbons, or cycloalkyl having from 3 to about 10 carbons, said alkyl and cycloalkyl groups being optionally substituted with one or more J groups;

$R_3$ is hydrogen, lower alkyl, aryl, heteroaryl, aralkyl, or heteroaralkyl;

t is 0 or 1;

J is halogen, alkyl, aryl, heteroaryl, amino optionally substituted with one to three aryl or lower alkyl groups, guanidino, alkoxycarbonyl, alkoxy, hydroxy, aryloxy, aralkyloxy, heteroalkyl, or carboxy; and Q has the formula:

$$-(O)_z-P(=O)(O)_m-R_4)(O)_n-R_5)$$

wherein:

m, n, and z are each independently 0 or 1;

$R_4$ and $R_5$ are each independently hydrogen, lower alkyl optionally substituted with J, aryl optionally substituted with J, aralkyl optionally substituted with j, or heteroaryl optionally substituted with J;

or $R_4$ and $R_5$ may be taken together along with the $-(O)_m-P(=O)-(O)_n-$ of Q to form a 5–8 membered heterocyclic ring optionally substituted with J;

or $R_4$ and $R_5$ taken together may form an aralkyl group; with the proviso that when t is 0, z is also 0; and with the proviso that when m and n are both 0, and t and z are both 1, $R_4$ and $R_5$ cannot be unsubstituted phenyl or halogen-substituted phenyl; and with the further proviso that $R_1$ cannot be methylene substituted with a carboxyl group.

In some preferred embodiments $R_1$ is aralkyl. In other preferred embodiments $R_2$ is alkyl. In further preferred embodiments $R_3$ is hydrogen. Preferably, Y is NH.

Also, in some preferred embodiments X is alkoxy, aralkyloxy, a carbohydrate moiety or, together with W, heteroalkylsulfonyl. In particularly preferred embodiments X is benzyloxy or t-butoxy.

In some preferred embodiments m and n are 1, and $R_4$ and $R_5$ are independently hydrogen, lower alkyl optionally substituted with J where J is preferably alkyl or aryl, aryl substituted with J where J is preferably halogen or alkyl, aralkyl optionally substituted with J where J is preferably alkyl or aryloxy, or $R_4$ and $R_5$ taken together with the $-(O)_m-P(=O)-(O)_n-$ of Q form a six membered ring that is substituted by J.

In particularly preferred embodiments $R_4$ and $R_5$ are independently H, methyl, butyl, 2-ethylhexyl, 2-cyclohexylethyl, 2-phenylethyl, 4-chlorophenyl, benzyl, 2-methylbenzyl, and 3-phenoxybenzyl, or $R_4$ and $R_5$, taken together with the $-(O)_m-P(=O)-(O)_n-$ of Q form a six-membered ring having the formula:

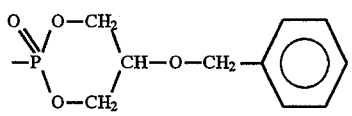

In other preferred embodiments m and n are 0, and $R_4$ and $R_5$ are independently aralkyl, lower alkyl optionally substituted with J where J is preferably alkyl, aryl or heteroalkyl, aryl optionally substituted with J where J is alkyl or alkoxy, or $R_4$ and $R_5$ taken together with the —(O)$_m$—P(=O)—(O)$_n$— of Q form a five membered ring.

In particularly preferred embodiments where m and n are 0, $R_4$ and $R_5$ are independently methyl, ethyl, pentyl, 2-phenylethyl, phenyl, 2-methylphenyl, 2-methoxyphenyl, 3-methoxyphenyl, 4-methoxyphenyl, and 3-morpholinopropyl, or $R_4$ and $R_5$ taken together with the —(O)$_m$—P(=O)—(O)$_n$— of Q form a five-membered ring having the formula:

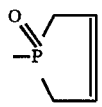

or the formula

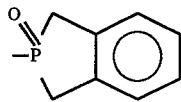

In further preferred embodiments m is 1, n is 0, and $R_4$ and $R_5$ are independently aryl, aralkyl, or lower alkyl optionally substituted with J where J is heteroalkyl. In particularly preferred embodiments where m is 1 and n is 0, $R_4$ and $R_5$ are methyl, ethyl, benzyl, phenyl, 2-morpholinoethyl, or 2-(2-oxopyrrolidin-1-yl)ethyl.

In some preferred embodiments, compounds of the invention have the Formula Ia:

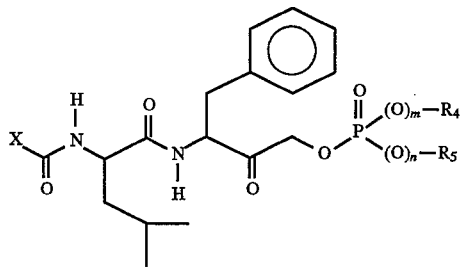

Ia wherein X, $R_4$, $R_5$, m and n are as previously defined.

In some preferred embodiments of Formula Ia, m and n are 1, and $R_4$ and $R_5$ are independently hydrogen, methyl, butyl, benzyl, 2-ethylhexyl or 2-phenylethyl. In other preferred embodiments of Formula Ia, $R_4$ and $R_5$ are independently benzyl or 2-phenylethyl.

In further preferred embodiments of Formula Ia, m and n are 0, and $R_4$ and $R_5$ are independently methoxyphenyl or 2-phenylethyl.

In other preferred embodiments of Formula Ia, X is benzyloxy or t-butoxy. In some preferred embodiments X, taken together with the carbonyl group of Formula Ia to which X is attached, is monoisopropylidine-2-keto-L-gulonyl or diisopropylidine-2-keto-L-gulonyl.

As used herein, the term "alkyl" is meant to include straight-chain, branched and cyclic hydrocarbon groups such as, for example, ethyl, isopropyl and cyclopropyl groups. Alkyl groups can contain one or two sites of unsaturation; i.e., carbon-carbon double or triple bonds. Preferred alkyl groups have 1 to about 10 carbon atoms. "Cycloalkyl" groups are cyclic alkyl groups. "Aryl" groups are aromatic cyclic compounds including but not limited to phenyl, tolyl, naphthyl, anthracyl, phenanthryl, pyrenyl, and xylyl. Preferred aryl groups include phenyl and naphthyl. The term "carbocyclic", as used herein, refers to cyclic groups in which the ring portion is composed solely of carbon atoms. The term "heterocyclic" refers to cyclic groups in which the ring portion includes at least one heteroatom such as O, N or S. "Heteroalkyl" groups are heterocycles containing solely single bonds within their ring portions, i.e. saturated heteroatomic ring systems. Heteroalkyl groups may contain sites of unsaturation outside their ring portions. Thus, for example, pyrrolidinonyl groups, which contain carbonyl carbon atoms within their ring systems, are heteroalkyl groups as defined herein. The term "lower alkyl" refers to alkyl groups of 1–4 carbon "halogen" term "halogen" refers to F, Cl, Br, and I atoms.

The term "aralkyl" denotes an alkyl group which is substituted with an aryl group, such as, for example, a benzyl group. Aralkyl groups can consist of two alkyl groups bound to a single aryl group, such as groups having the formula:

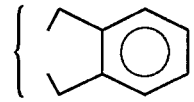

The term "aralkyloxy" denotes an aralkyl group attached through an oxygen atom. The term "heteroaryl" denotes aryl groups having one or more heteroatoms contained within an aryl ring. "Heteroaralkyl" groups are aralkyl groups which have one or more heteroatoms in their aryl ring portion. The term "carbohydrate" includes monosaccharides, disaccharides, and polysaccharides, as well as their protected derivatives, such as, for example, mono- and diisopropylidine derivatives.

Because the β-keto phosphates, β-keto phosphinates, β-keto phosphonates, α-keto phosphonates, α-keto phosphinates, and α-keto phosphine oxides of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. Inhibition of cysteine protease or serine protease activity can be measured by determining the rate of inactivation of a protease using a compound of the invention. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

The disclosed compounds of the invention are useful for the irreversible inhibition of cysteine proteases and serine proteases. As used herein, the terms "inhibit" and "inhibition" mean having an adverse effect on enzymatic activity. The term "irreversible," when used to modify "inhibit" and "inhibition" means that such adverse effect on catalytic activity can not be readily reversed. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients, e.g., other growth factors which could facilitate neuronal survival or axonal regeneration in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type and extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Compounds of the invention were prepared by the following procedures.

Starting Materials:

Phenylalanine chloromethylketone can be purchased from various commercial sources (e.g., BACHEM Bioscience, Inc.) and was used as received. Benzyloxycarbonyl and t-butoxycarbonyl protected dipeptide bromomethyl ketones were prepared from the corresponding diazomethylketones by treatment with HBr/AcOH or HBr (gas) according to the standard procedures cited and described in Harbeson, S. L. et al., *J. Med. Chem.* 1989, 32, 1378–1392. (Morpholinylsulfonyl)-L-leucine was prepared according to Repine's procedure (Repine, J. T. et al., *J. Med. Chem.*, 1992 35, 1032–1042). N-terminal protected dipeptide chloromethyl ketones were prepared from their corresponding N-terminal protected-L-leucine and phenylalanine chloromethylketone under isobutyl chloroformate mediated coupling conditions (Rich D. L. et al., *J. Med. Chem.* 1992 35, 3802–3812). N-t-Butoxycarbonyl-L-leucinal was prepared from t-butoxycarbonyl-L-leucine (Goel, O. P. et al., *Org. Syn.* 1993, Coll. Vol. VIII, 68). Dialkyl (2S)-2-(t-butoxycarbonylamino)-1-hydroxy-4-methylpentyl phosphonates were obtained by condensation of t-butoxycarbonyl-L-leucinal with corresponding dialkyl phosphites according to literature procedures (Texier-Boullet, F. et al., Synthesis 1982, 165). Two cyclic phosphinic acids were prepared according to Montchamp's procedure (Montchamp, J. et al., *J Org. Chem.* 1995, 60, 6076–6081). The disclosures of Harbeson et al., Repine et al., Rich et al., Goel et al., Texier-Boullet et al., and Montchamp et al. are hereby incorporated by reference in their entirety.

Analyses:

FAB mass spectra were obtained by M-Scan, Inc. Ion spray mass spectra were determined with Fisons VG platform mass spectrometer.

Example 1

Intermediate

Benzyloxycarbonyl-L-leucyl-L-phenylalanyl bromomethyl ketone (m.p. 135.5°–136.5° C.) was prepared by the procedure described by Harbeson et al., supra.

Example 2

Intermediate t-Butoxycarbonyl-L-leucyl-L-phenylalanyl bromomethyl ketone (m.p. 120°–122° C.) was prepared by the procedure described by Harbeson et al., supra.

Example 3

Intermediate

Diisopropylidine-2-keto-L-gulonyl-L-leucyl-L-phenylalanyl chloromethyl ketone (m.p. 74°–75° C.) was prepared by a modification of the procedure described by Rich et al., supra.

Example 4

Intermediate

Diisopropylidine-2-keto-L-gulonyl-L-leucyl-L-phenylalanyl iodomethyl ketone was prepared from diisopropylidine-2-keto-L-gulonyl-L-leucyl-L-phenylalanyl chloromethyl ketone with 1.5 eq. of NaI in acetone and used for the next step without purification.

Example 5

Intermediate

Morpholinylsulfonyl-L-leucyl-L-phenylalanyl chloromethyl ketone (m.p.145°–146.5° C.) was prepared by a modification of the procedure described by Rich et al., supra.

Example 6

Intermediate

Morpholinylsulfonyl-L-leucyl-L-phenylalanyl iodomethyl ketone was prepared from morpholinylsulfonyl-L-leucyl-L-phenylalanyl chloromethyl ketone with 1.5 eq. of NaI in acetone and used for the next step without purification.

Example 7

Intermediate

Diphenethyl phosphate:

A solution of 0.79 g (4.0 mmol) of N,N-diisopropyl methylphosphonamidic chloride in 0.6 mL of $CH_2Cl_2$ was stirred at 0° C. under $N_2$ as a mixture of phenethyl alcohol (0.50 g, 4.0 mmol) and pyridine (0.32 g, 1.0 eq.) in 0.6 mL of $CH_2Cl_2$ was added. The solution was warmed to room temperature and stirred overnight (~16 h). The solution was then cooled to 0° C. and 0.8 mL of MeOH and 2.4 mL of 30% $H_2O_2$ were slowly added. The mixture was warmed to room temperature and stirred for 5 hours, and the product was extracted with $CH_2Cl_2$ (2×10 mL). The combined organic layers were washed with 10% $Na_2SO_3$ (10 mL), 1N HCl (10 mL), brine (10 mL), dried over magnesium sulfate and concentrated. Flash chromatography (50% ethyl acetate in hexane) gave 0.51 (39%) of the bis(phenethyl) methyl phosphate as a clear oil.

A solution of 0.26 g (0.8 mmol) of bis(phenethyl) methyl phosphate in 3.2 mL of dry acetonitrile was stirred at 0° C. under $N_2$ while 0.23 mL (2.18 eq.) of TMSBr was added dropwise. The solution was stirred at 0° C. for 1.5 hours. The solvent was removed and the residue was dissolved in NaOH (1.0 eq.) in MeOH solution. After 30 minutes at room temperature, the solution was concentrated, and the white solid was taken up in ether (6.0 mL) and filtered to give sodium bis(phenethyl) phosphate.

A solution of sodium bis(phenethyl) phosphate (0.24 mg, 0.73 mmol) in 1.0 mL of water was stirred as 2.0 mL of concentrated hydrochloric acid (2.0 mL) was added. The organic layer was extracted with $CH_2Cl_2$ (3×6 mL) and dried over magnesium sulfate. Concentration gave 0.18 g (81%) of bis(phenethyl) phosphate. MS: 305 m/z (M–1).

Example 8

Intermediate

Bis(2-cyclohexylethyl) phosphate was prepared according to the general procedure given for bis(phenethyl) phosphate in Example 7. MS: 317 m/z (M–1).

Example 9

Intermediate

Bis(3-phenoxybenzyl) phosphate:

A solution of 0.79 ml (4.0 mmol) of N,N-diisopropyl methylphosphonamidic chloride in 0.6 mL of $CH_2Cl_2$ was stirred at 0° C. under $N_2$ as a mixture of 3-phenoxybenzyl alcohol (1.6 g, 8.0 mmol) and pyridine (0.32 g, 1.0 eq.) in 0.6 mL of $CH_2Cl_2$ was added. The solution was warmed to room temperature and stirred for 5 hours. The solution was then cooled to 0° C. and 0.8 mL of MeOH and 2.4 mL of 30%$H_2O_2$ were slowly added. The mixture was warmed to room temperature and stirred for 5 hours. The product was extracted with $CH_2Cl_2$ (2×10 mL). The combined organic layers were washed with 10% $Na_2SO_3$ (10 mL), 1N HCl (10 mL), brine (10 mL), dried over magnesium sulfate and concentrated. Flash chromatography (50% ethyl acetate in hexane) gave 0.51 g (39%) of the bis(3-phenoxybenzyl) methyl phosphate as a clear oil.

A solution of 0.48 g (1.0 mmol) of bis(3-phenoxybenzyl) methyl phosphate in 10 mL of toluene was stirred at rt under $N_2$ while 0.125 g (1.1 eq.) of 1,4-diazabicyclo[2.2.2]octane was added. The solution was refluxed for 4.0 hours. The solvent was removed and residue was diluted in 5% HCl solution (10 mL), extracted with EtOAc (3×10 mL) and dried over magnesium sulfate. Concentration gave 0.33 g (72%) of bis(3-phenoxybenzyl phosphate. MS: 461 m/z (M–1).

Example 10

Intermediate

Bis(2-methylbenzyl) phosphate was prepared according to the general procedure given for of bis(3-phenoxybenzyl) phosphate in Example 9. MS: 305 m/z (M–1).

Example 11

Intermediate

5-Benzyloxy-2-hydroxy-1,3,2-dioxaphosphorinane 2-oxide

A solution 0.5 g (2.75 mmol) of 2-benzyloxy-1,3-propanediol in 3.0 mL of pyridine was stirred at 0° C. under $N_2$ as 0.37 g (2.5 mmol) of methyl dichlorophosphate was added dropwise over 15 mins to keep the solution under 10° C. The cold bath was removed and the reaction mixture was stirred overnight at 20° C.(~14 h). The mixture was filtered, and washed with benzene (10 mL), and the filtrate was evaporated. The residue was dissolved in benzene: $CH_2Cl_2$ (1:1, 20 mL), washed with $H_2O$ (10 mL), saturated $NaHCO_3$ (10 mL), saturated NaCl (10 mL) and dried over magnesium sulfate. Evaporation afforded 0.26 g (40%) of 5-benzyloxy-2-methyl-1,3,2-dioxaphosphorinane-2-oxide.

A solution of 0.19 g (0.75 mmol) of (2benzyloxy) propylene methyl phosphate in 7.5 mL of toluene was stirred at rt under $N_2$ while 0.093 g (1.1 eq.) of 1,4-diazabicyclo [2.2.2]octane was added. The solution was refluxed for 4.0 hours. The solvent was removed and the residue was diluted in 5% HCl solution (10 mL), extracted with EtOAc (3×10 mL) and dried over magnesium sulfate. Concentration gave 0.14 g (74%) of 5-benzyloxy-2-hydroxy-1,3,2-dioxaphosphorinane-2-oxide. MS: 243 m/z (M-1).

Example 12

Intermediate

Methyl hydrogen N,N-diisopropylphosphonamidate:

A solution of 0.395 g (2.0 mmol) of methyl N,N-diisopropylphosphonamidic chloride in 0.3 mL of $CH_2Cl_2$ was stirred at 0° C. under $N_2$ as a mixture of benzyl alcohol (0.17 g, 1.6 mmol) and triethylamine (0.2 g, 1.0 eq.) in 0.3 mL of $CH_2Cl_2$ was added. The solution was warmed to room temperature and stirred overnight. The solution was cooled to 0° C. and 0.4 mL of MeOH and 1.2 mL of 30% $H_2O_2$ were slowly added. The mixture was warmed to room temperature and stirred for 0.5 hours. The product was extracted with $CH_2Cl_2$ (2×8 mL). The combined organic layers were washed with 10% $Na_2SO_3$ (8 mL), 1N HCl (8 mL), brine (8 mL), and dried over magnesium sulfate. Concentration gave 0.45 g (98%) of N,N-diisopropylmethyl benzyl phosphonamidate as a clear oil.

A suspension of 57 mg of 20% $Pd(OH)_2/C$ in a solution of N,N-diisopropylmethyl benzyl phosphonamidate (57 mg, 0.2 retool) in 3.0 mL of ethyl acetate was stirred under $H_2$ (1 atm) at room temperature for 2 hours. The catalyst was filtered through celite and the filtrate was concentrated to give 27 mg (69%) of the clean product.

Example 13

Intermediate

Bis(2-phenylethyl)phosphinic acid:

(2-Bromoethyl)benzene (6.8 mL, 9.21 g, 49.8 mmol) was added to magnesium turnings (1.20 g, 49.4 mmol) suspended in ether (20 mL) under nitrogen. When the reaction initiated, it was cooled and stirred for 40 minutes at 0° C., 40 minutes at 20° C., and 2.5 hours at reflux. Ether (10 mL) was added to the resulting Grignard reagent at 0° C. Dimethyl phosphite (1.22 mL, 1.86 g, 16.9 mmol) was added dropwise, resulting in a vigorous reaction and formation of a gelatinous precipitate.

The mixture was stirred with a glass rod, and then magnetically for 22 hours at 20° C. The heterogeneous mixture was cooled to 0° C., and 1M HCl (15 mL) was added slowly, followed by acidification with 6M HCl. The ether phase was separated, and the aqueous phase was extracted three times with EtOAc. The combined organic phases were rinsed with saturated NaCl and dried over $MgSO_4$ and the solvent evaporated to afford crude bis(2-phenylethyl)phosphinous acid (4.26 g) which was carried forward.

Hydrogen peroxide (0.45 mL, 30%, 4.36 mmol) was added dropwise over 1 minute to crude bis(2-phenylethyl) phosphinous acid (1.12 g, 4.34 mmol) in methanol (6.5 mL). After 16 hours, the solvent was evaporated. The residue was basified with 1M NaOH and extracted twice with hexanes. The aqueous layer was acidified with 12M HCl, and the precipitate was filtered, rinsed with water, and dried in vacuo, affording crude product (628 mg) mp 70°–77° C., which was recrystallized from hot ethanol-water (50:50) to give bis(2-phenylethyl)phosphinic acid (364 mg) as a white solid, mp 84°–87° C. NMR δ2.02 (4H, m), 2.94 (4H, q), 6.8 (1H, br. s), 7.24 (10H, m).

Analysis calculated for $C_{16}H_{19}O_2P$: C, 70.06; H, 6.98. Found: C, 69.86; H, 6.92.

Example 14

Intermediate

Bis[(2-methyl)phenyl]phosphinic acid was prepared according to the general procedure given for bis (2-phenylethyl)phosphinic acid in Example 13. MS: 245 m/z (M-1).

Example 15

Intermediate

Dipentylphosphinic acid was prepared according to the general procedure given for bis(2-phenylethyl)phosphinic acid in Example 13. MS: 189 m/z (M-1).

Example 16

Intermediate

Ethyl phenylphosphinate:

This compound was prepared according to the procedure described by Froestl, W. et al., *J. Med. Chem.*, 1995, 38, 3313–3331. From phenyl dichlorophosphine (10.0 g, 55.9 mmol), ethanol (9.1 ml, 156 mmol) and triethylamine (10.1 ml, 72.6 mmol) in anhydrous diethyl ether (100 ml) was obtained 7.7 g (81%) of the title compound as a colorless mobile oil following distillation; bp 72°–74° C. (0.15 mm Hg); analysis calculated for $C_8H_{11}O_2P$: C, 56.47; H, 6.53; P, 18.20; Found: C, 56.21; H, 6.47; P, 17.87.

Example 17

Intermediate

Ethyl (ethyl)(phenyl)phosphinate:

A slurry of sodium hydride (0.13 g of a 60% suspension in mineral oil, 3.2 mmol) in anhydrous THF (10 ml) was treated dropwise with a solution of ethyl phenylphosphinate (0.50 g, 2.9 mmol) over one hour via a syring pump. The mixture was allowed to stir an additional 30 minutes before the addition of ethyl iodide (0.26 ml, 3.2 mmol). After 45 minutes the reaction was quenched with 10% aqueous ammonium chloride (5 ml) and poured into a separatory funnel containing ethyl acetate (50 ml). The organic phase was washed with water, saturated aqueous sodium bicarbonate and brine before being dried over magnesium sulfate, filtered and concentrated to afford 0.30 g (52%) of the title compound as a colorless mobile oil following flash chromatography on silica gel (50% ethyl acetate/hexane); MS: 199 m/z (M+H)$^+$.

Example 18

Intermediate (Ethyl)(phenyl)phosphinic acid:

A solution of ethyl (ethyl)(phenyl)phosphinate (130 mg, 0.66 mmol) in ethanol (0.5 ml) was treated with 4N HCl (1 ml) and refluxed for 22 hours. Tlc analysis revealed some residual starting material. The ethanol was removed on the rotary evaporator, an additional aliquot of 4N HCl (1 ml) was added, and reflux was resumed for a further six hours whereupon tlc analysis revealed complete consumption of starting material. The mixture was lyophillized to afford 110 mg (99%) of the title compound as a white solid; MS: 171 m/z (M+H)$^+$; analysis calculated for $C_8H_{11}O_2P$: C, 56.47; H, 6.53; P, 18.20; Found: C, 56.23; H, 6.35; P, 18.52.

Example 19

Intermediate

1-Chloro-3-(N-morpholino)propane was prepared according to the procedure described in Adams, R. R. et al., *J. Amer. Chem. Soc.*, 1945, 67, 735–738. From morpholine (15.0 g, 172 mmol), and 1-bromo-3-chloropropane (11.3 ml, 115 mmol) in refluxing benzene (50 ml) was obtained 11.4 g (40%) of the title compound as a colorless mobile oil; bp 55°–58° C., 0.4 mmHg; MS: 164, 166 m/z (M+H)$^+$, chlorine isotope pattern.

This compound was seen to be somewhat unstable at ambient temperature and was stored at −10° C. and used as rapidly as possible or converted to the corresponding hydrochloride salt for long-term storage. The hydrochloride salt was prepared by treating an ethereal solution of the free base with 1N HCl in ether (1.1 equiv.), followed by filtration and washing with ether to give a fine white powder upon drying under vacuum; mp 176°–178° C.; analysis calculated for $C_7H_{15}Cl_2NO$: C, 42.01; H, 7.57; N, 7.00; Cl, 35.43; Found: C, 41.26; H, 7.37; N, 6.80; Cl, 35.47.

Example 20

Intermediate

Ethyl [3-(morpholin-4-yl)propyl](phenyl)phosphinate:

This compound was prepared using the general procedure described in Example 17 for the preparation of ethyl (ethyl)(phenyl)phosphinate, except that the reaction was conducted in anhydrous DMF instead of THF. From ethyl phenylphosphinate (0.5 g, 2.9 mmol) and 1-chloro-3-(N-morpholino)propane (0.6 g, 3.5 mmol) was obtained 0.32 g (37%) of the title compound as a colorless oil following flash chromatography on silica gel (10% methanol/ethyl acetate); MS: 298 m/z (M+H)$^+$, 320 m/z (M+Na)$^+$.

Example 21

Intermediate

[3-(Morpholin-4-yl)propyl](phenyl)phosphinic acid:

A solution of ethyl [3-(morpholin-4-yl)propyl](phenyl) phosphinate (300 mg, 1.0 mmol) in 4N HCl (5 ml) was refluxed for 18 hours. Lyophilization afforded 310 mg (100%) of the title compound as an amorphous hygroscopic solid; MS: 270 m/z (M+H)$^+$.

Example 22

Intermediate

2-Hydroxy-1H-phosphindoline 2-oxide was prepared by the procedure described by Montchamp et al., supra. MS: 167 m/z (M−1).

Example 23

Intermediate

1-Hydroxyphosphol-3-ene 1-oxide was prepared by the procedure described by Montchamp et al., supra. MS: 117 m/z (M−1).

Example 24

Intermediate

Dibenzyl phenylphosphonate:

A stirred solution of phenylphosphonic acid (1.0 g, 6.3 mmol), benzyl alcohol (1.6 ml, 15.8 mmol) and triphenylphosphine (4.2 g, 15.8 mmol) in anhydrous THF (60 ml) under $N_2$ was treated dropwise with diethyl azodicarboxylate (2.5 ml, 15.8 mmol) over five minutes. The mixture was stirred for two hours before being concentrated under vacuum. The residue was stirred with acetone-hexane (15 ml, 1/1) at 5° C. for 1–2 hours and the resulting precipitate of triphenylphosphine oxide was collected by suction filtration and discarded. The filtrate was concentrated in vacuo and the residue was stirred a second time with acetone-hexane (15 ml, 1/1) at 5° C. for 1–2 hours to provide an additional crop of triphenylphosphine oxide following filtration. The filtrate was concentrated as before to give 5.2 g of the crude product as a nearly colorless oil. Flash chromatography (silica gel, 10–40% ethyl acetate/hexane) gave 1.6 g (76%) of the title compound as a colorless oil. NMR δ7.85–7.30 (15H, m), 5.15–5.00 (4H, m); MS: 339 m/z (M+H), 361 m/z (M+Na).

Example 25

Intermediate

Monobenzyl phenylphosphonate:

A solution of dibenzyl phenylphosphonate (340 mg, 1.0 retool) and 1,4-diazabicyclo[2.2.2]octane (124 mg, 1.1 mmol) in toluene (5 ml) was refluxed for 12–18 hours. Ethyl acetate (25 ml) was added and the mixture was washed with 2N HCl (2×15 ml), water (15 ml) and finally brine (15 before being dried ($MgSO_4$), filtered and concentrated to provide 215 mg (87%) of the title compound as a colorless oil which was used without further purification. NMR δ7.85–7.25 (10H, m), 5.05 (2H, d); MS: 248 m/z (M+H), 271 m/z (M+Na).

Example 26

Intermediate

Dibenzyl methylphosphonate was prepared by the general procedure described for dibenzyl phenylphosphonate, Example 24. From methylphosphonic acid (1.0 g, 10.4 mmol), benzyl alcohol (2.7 ml, 26 mmol), triphenylphosphine (678 g, 26 mmol) and diethyl azodicarboxylate (4.1 ml, 26 mmol) in anhydrous THF (100 ml) was obtained 1.7 g (58%) of the title compound as a colorless oil following flash chromatography on silica gel (30% ethyl acetate/hexane). MS: 277 m/z $(M+H)^+$, 299 m/z $(M+Na)^+$.

Example 27

Intermediate

Monobenzyl methylphosphonate was prepared by the general procedure described for the preparation of monobenzyl phenylphosphonate in Example 25. From dibenzyl methylphosphonate (500 mg, 1.8 mmol), and 1,4-diazabicyclo [2.2.2]octane (223 mg, 2.0 mmol) in refluxing toluene (10 ml) after 21 hours was obtained 80 mg (24%) of the title compound as a pale yellow oil which was used without further purification. MS: 185 m/z (M−H).

Example 28

Intermediate

Benzyl 2-(morpholin-4-yl)ethyl phenylphosphonate:

A mixture of monobenzyl phenylphosphonate (115 mg, 0.46 mmol), N-(2-chloroethyl)morpholine hydrochloride (95 mg, 0.51 mmol) and potassium carbonate (140 mg, 1.0 mmol) in anhydrous DMF was stirred at 65° C. for 22 hours. Following dilution with ethyl acetate (40 ml), the mixture was washed with water four times and finally brine before being dried over magnesium sulfate, filtered and concentrated to leave 124 mg (74%) of the title compound as a pale yellow oil which was used without further purification. MS: 362 m/z $(M+H)^+$.

Example 29

Intermediate 2-(Morpholin-4-yl)ethyl phenylphosphonate:

A mixture of benzyl 2-(morpholin-4-yl)ethyl phenylphosphonate (110 mg, 0.30 mmol) and 10% Pd/C (100 mg) in ethanol (5 ml) was hydrogenated under 40 psi $H_2$ on a Paar apparatus for two hours at ambient temperature. Filtration and concentration afforded 76 mg of the title compound as a colorless viscous oil which was used without further purification. MS: 272 m/z $(M+H)^+$.

Example 30

Intermediate

Benzyl phenylphosphonic chloride:

A solution of dibenzyl phenylphosphonate (1.5 g, 4.4 mmol) and diazabicyclo[2.2.2]octane (0.55 g, 4.9 mmol) in toluene (35 ml) was refluxed for 5 hours. The mixture was cooled in an ice-water bath and treated with one drop of anhydrous DMF followed by oxalyl chloride (0.81 ml, 9.3 mmol). After being stirred for 30 minutes the mixture was filtered and concentrated to give 0.75 g (63%) of the title compound as a pale yellow oil which was used without further purification. MS: 267 m/z $(M+H)^+$, 289 m/z $(M+Na)^+$.

Example 31

Intermediate

Benzyl 2-(2-oxopyrrolidin-1-yl)ethyl phenylphosphonate:

An ice-cooled solution of 1-(2-hydroxyethyl)-2-pyrrolidinone (160 mg, 1.2 mmol) and triethylamine (0.17 ml, 1.2 mmol) in dichloromethane (5 ml) was treated dropwise over 5 minutes with a solution of benzyl phenylphosphonic chloride (330 mg, 1.2 mmol) in dichloromethane (5 ml). The mixture was allowed to slowly warm to ambient temperature while stirring overnight. The mixture was poured into a separatory funnel containing ethyl acetate (50 ml) and water (25 ml). The organic phase was washed once more with water and finally brine before being dried over magnesium sulfate, filtered and concentrated to afford 200 mg (45%) of the title compound as a yellow mobile oil. MS: 360 m/z $(M+H)^+$, 382 m/z $(M+Na)^+$.

Example 32

Intermediate 2-(2-Oxopyrrolidin-1-yl)ethyl phenylphosphonic acid was prepared according to the general procedure described for the preparation of 2-(morpholin-4-yl)ethyl phenylphosphonate in Example 29 From benzyl 2-(2-oxopyrrolidin-1-yl)ethyl phenylphosphonate (170 mg, 0.47 mmol) and 10% Pd/C (100 mg) in ethanol (15 ml) was obtained 107 mg (84%) of the title compound. MS: 270 m/z $(M+H)^+$, 292 m/z $(M+Na)^+$.

Example 33

Methods for Preparing Inhibitors

Methods A, B, C, D and E are representative methods for preparing compounds of the invention.

Method A: To a solution of the appropriate bromo or iodoketone (0.1–0.2 mmol) in 1.0–2.0 mL of DMF was added anhydrous potassium fluoride (3.5 eq.) under $N_2$. After the mixture was stirred at room temperature for 5 minutes, a phosphate, phosphonate, phosphinic acid, or phosphonamidate (1.2 eq.) was added, and the mixture was stirred for 3–72 hours. The reaction mixture was diluted with $CH_2Cl_2$ and filtered through celite. The solution was washed with water, 5% $NaHCO_3$ solution, 5% aqueous citric acid, brine and dried over magnesium sulfate. Purification by flash chromatography or crystallization afforded the desired product.

Method B: A solution of the appropriate bromo or iodoketone (0.1–0.2 mmol) in 0.5–1.0 mL of $CH_2Cl_2$ was stirred at 0° C. under Ar while diisopropylethylamine (3.3 eq.) was added dropwise by syringe. After 5 minutes, a phosphate or phosphinic acid (1.2 eq.) was added, and the reaction was warmed to room temperature and stirred for 3–24 hours. The reaction was diluted with ethyl acetate and washed with 5% $NaHCO_3$ solution, 5% aqueous citric acid, brine and dried over $MgSO_4$. Purification by flash chromatography or crystallization afforded the desired product.

Methods C, D and E are representative methods for preparing compounds of the invention from dialkyl (2S)-2-(t-butoxycarbonylamino)-1-hydroxy-4-methylpentyl phosphonates.

Method C: Dialkyl (2S)-2-(t-butoxycarbonylamino)-1-hydroxy-4-methylpentyl phosphonates were prepared from Boc-L-Leucinal with dialkyl phosphites by a modification of the procedure described by Texier-Boullet et al., supra.

Method D: The Boc protecting group was removed by treating the dialkyl (2S)-2-(t-butoxycarbonylamino)-1-hydroxy-4-methylpentyl phosphonate with 4N HCl in dioxane. The solvent was evaporated in vacuo, and the residue was triturated with diethyl ether. The crude white solid, 2-amino-1-hydroxy-4-methylpentyl phosphonate HCl salt, was used directly for the next step.

To a solution of Cbz-Leu-OH (1.0 mmol) in DMF (5 mL) was added 2-amino-1-hydroxy-4-methylpentyl phosphonate HCl salt (1.0 mmol), iPr$_2$NEt (1.0 mmol), HOBt (1.0 mmol) and DCC or BOP (1.0 mmol) at 0° C. The reaction mixture was stirred at 0° C. for 5 min. and for 2–24 h at room temperature. Dicyclohexylurea was filtered off (when DCC was used) and the solvent was evaporated. The residue was dissolved in ethyl acetate (20 mL) and washed with 3% of citric acid, 5% of NaHCO$_3$, and brine. The organic layer was dried over MgSO$_4$. The crude material was purified by flash chromatography (ethyl acetate in hexane).

Method E: A solution of Cbz-L-leucyl-L-2-amino-(R,S)-1-hydroxy-4-methylpentylphosphonate (0.2 mmol) and t-BuOH (0.41 retool) in CH$_2$Cl$_2$ (5 mL) was stirred as Dess-Martin periodinane (0.4 mmol) was added. The reaction was stirred at room temperature for 2–3 h. The reaction mixture was diluted with CH$_2$Cl$_2$ and filtered through celite. The filtrate was washed with 10% Na$_2$S$_2$O$_3$ and dried over MgSO$_4$ or directly concentrated to dryness. The crude product was purified by preparative HPLC or crystallization. The following Examples list method, starting materials, reaction times, purification methods, yields, physical properties, elemental analyses and/or mass spectra.

Example 34

Dibenzyl (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; dibenzyl phosphate (Aldrich Chemical Co.); 24 h; flash chromatography (30% ethyl acetate in hexane); yield 44%; mp 117°–118° C.; FABMS: 687 m/z (M+H).

Analysis calculated for C$_{38}$H$_{43}$N$_2$O$_8$P: C, 66.46; H, 6.31; N, 4.08. Found: C, 66.18; H, 5.94; N, 4.41.

Example 35

Dibenzyl (3S)-[3-[(N-t-Butoxycarbonyl-L-leucyl)amino]-2-oxo-4-phenylbutyl] phosphate:

Method A; Boc-L-leucyl-L-phenylalanyl bromomethyl ketone; dibenzyl phosphate; 17 hours; flash chromatography (2:1 ethyl acetate: hexane); yield 46%; mp 84°–85° C.; MS: 653 m/z (M+H); 675 m/z (M+Na).

Analysis calculated for C$_{35}$H$_{45}$N$_2$O$_8$P: C, 64.40; H, 6.95; N, 4.29. Found: C, 64.32; H, 7.10; N, 4.75.

Example 36

Dibenzyl (3S)-[3-[(N-morpholinylsulfonyl-L-leucyl)amino]-2-oxo-4-phenylbutyl] phosphate:

Method A; morpholinylsulfonyl-L-leucyl-L-phenylalanyl iodomethyl ketone; dibenzyl phosphate; 24 hours; flash chromatography (50% ethyl acetate in hexane); yield 38%; mp 52°–52.5° C.; MS: 702 m/z (M+H); 724 m/z (M+Na).

Analysis calculated for C$_{34}$H$_{44}$N$_3$O$_9$PS: C, 58.19; H, 6.32; N, 5.99. Found: C, 57.25; H, 6.25; N, 6.31.

Example 37

Dibenzyl (3S)-[3-[(N-diisopropylidine-2-keto-L-gulonyl-L-leucyl)amino]-2-oxo-4-phenylbutyl] phosphate:

Method A; Diisopropylidine-2-keto-L-gulonyl-L-leucyl-L-phenylalanyl iodomethyl ketone; dibenzyl phosphate; 20 hours; flash chromatography (50% ethyl acetate in hexane); yield 41%; mp 61–62° C; MS: 809 m/z (M+H);

Analysis calculated for C$_{42}$H$_{53}$N$_2$O$_{12}$P.0.7 H$_2$O: C, 61.40; H, 6.67; N, 3.41. Found: C, 61.26; H, 6.56; N, 3.30.

Example 38

Dibenzyl (3S)-[3-[(N-monoisopropylidine-2-keto-L-gulonyl-L-leucyl)amino]-2-oxo-4-phenylbutyl] phosphate):

A solution of 12.1 mg (0.015 mmol) of dibenzyl (3S)-[3-[(N-diisopropylidine-2-keto-L-gulonyl-L-leucyl)amino]-2-oxo-4-phenylbutyl] phosphate in 0.5 mL of THF was stirred at room temperature as 0.5 mL of 1.0N HCl was added. The mixture was stirred at room temperature for 4 hours. The solution was diluted with 15 mL of CH$_2$Cl$_2$, washed with water (2×5mL), brine (5 mL), dried over magnesium sulfate. Concentration of the solution gave 8.1 mg (70%) of the product. MS: 769 m/z (M+H); 791 m/z (M+Na).

Example 39

Bis(2-methylbenzyl) (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; bis(2-methylbenzyl) phosphate; 24 h; flash chromatography (50% ethyl acetate in hexane); yield 15%; mp 87.5°–88.5° C.; MS: 737 m/z (M+Na).

Example 40

Bis(3-phenoxybenzyl) (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; bis(3-phenoxybenzyl) phosphate; 20 h; flash chromatography (50% ethyl acetate in hexane); yield 20%; mp 71.5°–73° C.; MS: 871 m/z (M+H); 893 m/z (m+Na).

Example 41

Dihydrogen (3S)-[3-[(N-t-Butoxycarbonyl-L-leucyl)amino]-2-oxo-4-phenylbutyl] phosphate:

A suspension of 30 mg of 20% Pd(OH)$_2$ in a solution of dibenzyl (3S)-[3-[(N-t-Butoxycarbonyl-L-leucyl)amino]-2-oxo-4-phenylbutyl] phosphate (30 mg, 0.046 mmol) in 1.0 mL of ethyl acetate was stirred under H$_2$ (1 atm) at room temperature for 4 hours. The catalyst was filtered through Celite™ and the filtrate was concentrated to give the crude product. Flash chromatography (10% MeOH in CH$_2$Cl$_2$) gave 8 mg of pure product. MS: 471 m/z (M−1).

Example 42

Dimethyl (3S)-[3-[(N-Benzyloxycarbonyl-L-leucyl)amino]-2-oxo-4-phenylbutyl] phosphate:

Method B; Cbz-L-leucyl-L-phenylalanyl bromomethyl ketone; dimethyl phosphate (Pfaltz & Bauer Inc.); 24 hours; flash chromatography (50% ethyl acetate in hexane); yield 29%; mp 87°–88.5° C.; MS: 535 m/z (M+H); 557 m/z (M+Na).

Example 43

Dibutyl (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; dibutyl phosphate (Fluka Chemical Co.); KF/AlO3 (substituted for KF, 40% Aldrich Chemical Co.); 30 h; flash chromatography (30% ethyl acetate in hexane) and recrystallization from ether/petroleum ether; yield 35%; mp 76°–77° C.; MS: 619 m/z (M+H); 641 m/z (M+Na).

Analysis calculated for $C_{32}H_{47}N_2O_8P$: C, 62.12; H, 7.66; N, 4.53. Found: C, 62.21; H, 7.64; N, 4.48.

Example 44

Bis(2-ethylhexyl) (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; bis(2-ethylhexyl) phosphate (Aldrich Chemical Co.); 24 h; flash chromatography (30% ethyl acetate in hexane); yield 25%; mp 88°–89.5° C.; FABMS: 731 m/z (M+H).

Analysis calculated for $C_{40}H_{63}N_2O_8P$: C, 65.73; H, 8.69; N, 3.83. Found: C, 65.64; H, 8.42; N, 3.96.

Example 45

Bis(2-cyclohexylethyl) (3S)-[3-[(N-t-Butoxycarbonyl-L-leucyl)amino]-2-oxo-4-phenylbutyl] phosphate:

Method A; Cbz-L-leucyl-L-phenylalanyl bromomethyl ketone; bis(2-cyclohexylethyl) phosphate; 24 h; flash chromatography (50% ethyl acetate in hexane); yield 13%; mp 51°–52.5° C.; FABMS: 715 m/z (M+Na).

Example 46

Diphenethyl (3S)-[3-[(N-Benzyloxycarbonyl-L-leucyl)amino]-2-oxo-4-phenylbutyl] phosphate:

Method A; Cbz-L-leucyl-L-phenylalanyl bromomethyl ketone; bis(phenethyl) phosphate; 24 hours; flash chromatography (50% ethyl acetate in hexane); yield 62%; m.p. 89°–90° C.; MS: 715 m/z (M+H); 737 m/z (M+Na).

Analysis calculated for $C_{40}H_{47}N_2O_8P$: C, 67.20; H, 6.63; N, 3.92. Found: C, 67.04; H, 6.64; N, 3.85.

Example 47

1-[(3S)-3-[(N-Benzyloxycarbonyl-L-leucyl)amino]-2-oxo-4-phenylbutyl]oxy]-5-benzyloxy-1,3,2-dioxaphosphosrinane 2-oxide Method A; Cbz-L-leucyl-L-phenylalanyl bromomethyl ketone; 5-benzyloxy-2-hydroxy-1,3,2-dioxaphosphorinane 2-oxide; 16 hours; crystallization from ethyl acetate in hexane; yield 10%; m.p. 150°–151° C.; MS: 675 m/z (M+Na).

Example 48

Benzyl (3S)-[3-[(N-benzyloxycarbonyl-L-leucyl)amino]-2-oxo-4-phenylbutyl] methylphosphonate:

Method A; Cbz-L-leucyl-L-phenylalanylbromomethyl ketone; monobenzyl methylphosphonate; recrystallization (ethyl acetate/hexane; yield 22%), mp 165°–167° C. Analysis calculated for $C_{32}H_{39}N_2O_7P$: C, 64.62; H, 6.62. Found: C, 64.54; H, 6.30.

Example 49

Benzyl (3S)-[3-[(N-Benzyloxycarbonyl-L-leucyl)amino]-2-oxo-4-phenylbutyl]phenylphosphonate:

Method A; Cbz-L-leucyl-L-phenylalanyl bromomethyl ketone; monobenzyl phenylphosphonate; recrystallization (ethyl acetate/hexane; yield 46%), mp 111°–114° C., NMR δ7.90–7.00 (20H, m), 6.59 (1H, m), 5.25–4.50 (8H, m), 4.15–4.05 (1H, m), 3.18–3.05 (1H, m), 2.97–2.83 (1H, m), 1.62–1.25 (3H, m), 0.95–0.80 (6H, m), MS: 657 m/z (M+H), 679 m/z (M+Na).

Example 50

2-(Morpholin-4-yl)ethyl (3S)-[3-[(N-benzyloxycarbonyl-L-leucyl)amino]-2-oxo-4-phenylbutyl] phenylphosphonate hydrochloride:

Method A; Cbz-L-leucyl-L-phenylalanylbromomethyl ketone; 2-(morpholin-4-yl)ethyl phenylphosphonate; 7 hours; reverse-phase HPLC; yield 12% of a white amorphous solid which was extremely hygroscopic. A sample (9 mg) was dissolved in acetonitrile (2 ml) and 2N HCl and subjected to lyophilization to give 8 mg of the title compound as a white amorphous powder. MS: 680 m/z (M+H)⁺.

Example 51

(3S)-[3-[(N-Benzyloxycarbonyl-L-leucyl)amino]-2-oxo-4phenylbutyl] 2-(2-oxopyrrolidin-1-yl)ethyl phenylphosphonate:

Method A; Cbz-L-leucyl-L-phenylalanylbromomethyl ketone; 2-(2-oxopyrrolidin-1-yl)ethyl phenylphosphonic acid; 24 hours; precipitation from diethyl ether; yield 17%; MS: 678 m/z (M+H)⁺, 700 m/z (M+Na)⁺.

Example 52

(3S)-[3-[(N-Benzyloxycarbonyl-L-leucyl)amino]-2-oxo-4-phenylbutyl] dimethylphosphinate:

Method A; Cbz-L-leucyl-L-phenylalanyl bromomethyl ketone; dimethylphosphinic acid; 24 hours; crystallization (diethyl ether and petroleum ether); yield; 66% mp 121°–122° C.; MS: 503 m/z(M+H).

Analysis calculated for $C_{26}H_{35}N_2O_6P$: C, 62.14; H, 7.02; N, 5.57. Found: C, 62.14; H, 6.85; N, 5.63.

Example 53

(3S)-[3-[(N-Benzyloxycarbonyl-L-leucyl)amino]-2-oxo-4phenylbutyl] dipentylphosphinate:

Method A; Cbz-L-leucyl-L-phenylalanyl bromomethyl ketone; dipentylphosphinic acid; 48 hours; flash chromatography (2:1 ethyl acetate in hexane); yield; 10% mp 112.5°–114° C.; MS: 615 m/z(M+H).

Example 54

(3S)-[3-[(N-Benzyloxycarbonyl-L-leucyl)amino]-2-oxo-4phenylbutyl] bis(2-phenylethyl)phosphinate:

Method A; Cbz-L-leucyl-L-phenylalanyl bromomethyl ketone; bis(2-phenylethyl)phosphinic acid; 4.5 hours; flash chromatography (EtOAc-hexanes 75:25); yield 72% mp 95°–100° C. (softens 80° C.). MS: 683 (M+H), 705 (M+Na). NMR δ0.91 (6H, m), 1.50 (3H, m), 2.09 (4H, m), 2.89 (4H, m), 3.14 (1H, m), 4.16 (1H, m), 4.54 (1H, m), 5.08 (2H, ab-q), 5.10 (1H, d), 6.84 (1H, d), 7.24 (20H, m).

Analysis calculated for $C_{40}H_{47}N_2O_6P$: C, 70.36; H, 6.94; N, 4.10. Found: C, 69.97; H, 7.02; N, 3.98.

Example 55

(3S)-[3-[(N-Benzyloxycarbonyl-L-leucyl)amino]-2-oxo-4phenylbutyl] bis(2-methylphenyl)phosphinate:

Method A; Cbz-L-leucyl-L-phenylalanyl bromomethyl ketone; bis(2-methylphenyl)phosphinic acid; 15 hours; flash chromatography (50% ethyl acetate in hexane); yield; 6% mp 58°–60.5° C.; MS: 655 (M+H).

Example 56

(3S)-[3-[(N-t-Butoxycarbonyl-L-leucyl)amino]-2-oxo-4phenylbutyl] bis(2-methylphenyl)phosphinate:

Method A; Boc-L-leucyl-L-phenylalanyl bromomethyl ketone; bis(2-methylphenyl)phosphinic acid; 24 hours; flash chromatography (50% ethyl acetate in hexane); yield; 6.5% mp 69°–71° C.; MS: 621 (M+H).

Example 57

(3S)-[3-[(N-Benzyloxycarbonyl-L-leucyl)amino]-2-oxo-4phenylbutyl] bis(4-methoxyphenyl)phosphinate:

Method A; Cbz-L-leucyl-L-phenylalanyl bromomethyl ketone; bis(4-methoxyphenyl)phosphinic acid; 3 hours; flash chromatography (2.5:1 ethyl acetate in hexane); yield 60%; m.p. 58°–59° C.; MS: 686 m/z (M+H); 709 m/z (M+Na).

Analysis calculated for $C_{38}H_{43}N_2O_8P \cdot 0.5\ H_2O$: C, 65.60; H, 6.37; N, 4.03. Found: C, 65.71; H, 6.31; N, 4.08.

Example 58

(3S)-[3-[(N-Benzyloxycarbonyl-L-leucyl)amino]-2-oxo-4-phenylbutyl] (2-methoxyphenyl)(phenyl)phosphinate:

Method B; Cbz-L-leucyl-L-phenylalanyl bromomethyl ketone; (2-methoxyphenyl)-phenylphosphinic acid; 24 h; crystallization from ether/petroleum ether; yield 38%; m.p.120°–121° C.; MS: 657 m/z (M+H); 679 m/z (M+Na).

Analysis calculated for $C_{37}H_{41}N_2O_7P$: C, 67.67; H, 6.29; N, 4.27. Found: C, 67.11; H, 6.15; N, 4.13.

Example 59

(3S)-[3-[(N-Benzyloxycarbonyl-L-leucyl)amino]-2-oxo-4-phenylbutyl] (3-methoxylphenyl)(phenyl)phosphinate:

Method A; Cbz-L-leucyl-L-phenylalanyl bromomethyl ketone; (3-methoxylphenyl)(phenyl)phosphinic acid; 17 hours; crystallization (diethyl ether in pentane); yield; 97% mp 65°–67° C.; MS: 657 (M+H).

Example 60

(3S)-[3-[(N-Benzyloxycarbonyl-L-leucyl)amino]-2-oxo-4-phenylbutyl] (ethyl)(phenyl)phosphinate:
Method A; Cbz-L-leucyl-L-phenylalanylbromomethyl ketone; (ethyl)(phenyl)phosphinic acid; 15 hours; recrystallization (ethyl acetate/hexane); yield 50%; mp 141°–144° C.; analysis calculated for $C_{32}H_{39}N_2O_7P$: C, 66.41; H, 6.81; N, 4.84; P, 5.35; Found: C, 66.32; H, 6.72; N, 4.74; P, 5.21.

Example 61

(3S)-[3-[(N-Benzyloxycarbonyl-L-leucyl) amino]-2-oxo-4-phenylbutyl] [3-(morpholin-4 -yl)propyl](phenyl)phosphinate:

Method B (but conducted in DMF); Cbz-L-leucyl-L-phenylalanylbromomethyl ketone; [3-(morpholin-4-yl)propyl](phenyl)phosphinic acid; 18 hours; flash chromatography (silica gel, 10% methanol/ethyl acetate); yield 43%; MS: 270 (M+H)$^+$.

Example 62

(3S)-2-[3-[(N-Benzyloxycarbonyl-L-leucyl)amino]-2-oxo-4-phenylbutyl] 1H-phosphindoline 2-oxide:

Method A; Cbz-L-leucyl-L-phenylalanyl bromomethyl ketone; 2-hydroxy-1H-phosphinodoline 2-oxide; 15 hours; crystallization (ethyl acetate in hexane); yield; 21%; MS: 699 m/z(M+Na).

Example 63

(3S)-1-[[3-[(N-Benzyloxycarbonyl-L-leucyl)amino]-2-oxo-4-phenylbutyl]oxy]phosphol-3-ene 1-oxide:

Method A; Cbz-L-leucyl-L-phenylalanyl bromomethyl ketone; 1-hydroxyphosphol-3-ene 1-oxide; 17 hours; tritrated from diethyl ether; yield; 47% mp 136°–137.5° C.; MS: 527 m/z (M+H).

Example 64

Ethyl (3S)-[3-[(N-benzyloxycarbonyl-L-leucyl)amino]-2-oxo-4phenylbutyl](phenyl)phosphinate:

Method A; Cbz-L-leucyl-L-phenylalanylbromomethyl ketone; ethyl phenylphosphinate; 22 hours; flash chromatography (silica gel, 33% ethyl acetate/hexane); yield 37%; MS: 579 m/z (M+H)$^+$; 601 m/z (M+Na)$^+$.

Example 65

Methyl Hydrogen N-Benzyloxycarbonyl-L-leucyl-L-leucylphosphonate was prepared from method C-E.

Method C; Boc-Leu-H; dimethyl phosphite; 24 h; yield; 92%; MS: 348 m/z (M+Na).

Method D; Cbz-Leu-OH, dimethyl 2-amino-1-hydroxy-4-methylpentyl phosphonate HCl salt; 24 h; flash chromatography (5% MeOH in $CH_2Cl_2$); yield 14%; product; Dimethyl Cbz-L-leucyl-L-2-amino-(R,S)-1-hydroxy-4-methylpentyl phosphonate; MS: 473 m/z (M+H).

A solution of dimethyl Cbz-L-leucyl-L-2-amino-(R,S)-1-hydroxy-4-methylpentyl phosphonate (0.3 mmol, 142 mg) in $CH_3CN$ (1.2 mL) was stirred at room temperature under Ar as lithium bromide (0.95 mmol, 25 mg) was added. The reaction mixture was stirred overnight. The solvent was removed and the crude product was used directly for the next step.

Method E; methyl hydrogen Cbz-L-leucyl-L-2-amino-(R, S)-1-hydroxy-4-methylpentyl phosphonate; Dess-Martin periodinane; 16 h; yield 65%; mp 57° C. (dec.); Ms 455 m/z (M–H).

Analysis calculated for $C_{21}H_{33}N_2O_7P$: C, 55.24; H, 7.29; N, 6.14. Found: C, 55.44; H, 7.02; N, 6.03.

Example 66

Dibutyl N-Benzyloxycarbonyl-L-leucyl-L-leucylphosphonate:

Method C; Boc-Leu-H; dibutyl phosphite; 24 h; yield; 47%; MS: 410 m/z (M+1).

Method D; Cbz-Leu-OH, dibutyl 2-amino-1-hydroxy-4-methylpentyl phosphonates HCl salt; 36 h; flash chromatography (40% hexane in EtOAc); yield 71%; product; dibutyl Cbz-L-leucyl-L-2-amino-(R,S)-1-hydroxy-4-methylpentyl phosphonate; MS: 557 m/z (M+H); 579 m/z (M+Na).

Method E; Dibutyl Cbz-L-leucyl-L-2-amino-(R,S)-1-hydroxy-4-methylpentyl phosphonate; Dess-Martin periodinane; 5 h; yield 13% (after prep. HPLC); Ms 555 m/z (M+H); 577 m/z (M+Na).

Example 67

[Benzyloxycarbonyl-L-leucyl-L-leucyl]bis(4-chlorophenyl) phosphine oxide:

Method C; t-Boc-Leu-H; bis(4-chlorophenyl)phosphine oxide; 2.5 hours; yield 83% (2S)-[2-[(t-Butoxycarbonyl) amino]-1-hydroxy-4-methylpentyl]bis(4-chlorophenyl) phosphine oxide; MS: 486, 488 m/z (M+H)$^+$, dichloro isotope pattern.

(2S)-[2-[(t-butoxycarbonyl)amino]-1-hydroxy-4-methylpentyl]bis(4-chlorophenyl)phosphine oxide was treated with 25% trifluoroacetic acid in dichloromethane for 1 hour. Yield 97%; (2S)-(2-Amino-1-hydroxy-4-methylpentyl)bis(4chlorophenyl)phosphine oxide; MS: 386, 388 m/z (M+H)$^+$, dichloro isotope pattern.

Method D; Cbz-Leu-OH; (2S)-[2-amino-1-hydroxy-4-methylpentyl]bis(4-chlorophenyl)phosphine oxide; 14 hours; flash chromatography (silica gel, 50% ethyl acetate/hexane); yield 48% [Benzyloxycarbonyl-L-leucyl-L-2-amino-(R,S)-1-hydroxy-4-methylpentyl]bis(4-chlorophenyl)phosphine oxide; MS: 633, 635 m/z (M+H)$^+$; 655, 657 m/z (M+Na)$^+$, dichloro isotope pattern.

Method E; [Benzyloxycarbonyl-L-leucyl-L-2-amino-(R,S)-1-hydroxy-4-methylpentyl]bis(4-chlorophenyl) phosphine oxide; Dess-Martin periodinane; one hour; yield 30%; MS: 631, 633 m/z (M+H)$^+$; 654, 656 m/z (M+Na)$^+$, dichloro isotope pattern.

Example 68

Ethyl N-benzyloxycarbonyl-L-leucyl-L-leucyl(phenyl) phosphinate:

Method C; Cbz-Leu-H; ethyl phenylphosphinate; 23 hours; yield 75%; Ethyl (2S)-[2-[(benzyloxycarbonyl) amino]-1-hydroxy-4-methylpentyl](phenyl)phosphinate; MS: 420 m/z (M+H)$^+$; 442 m/z (M+Na)$^+$.

Hydrogenation over 10% Pd/C in ethanol, afforded 81% ethyl (2S)-(2-amino-1-hydroxy-4-methylpentyl)(phenyl) phosphinate; MS: 286 m/z (M+H)$^+$.

Method D; Cbz-Leu-OH; ethyl (2S)-(2-amino-1-hydroxy-4-methylpentyl)(phenyl)phosphonate; 4 hours; flash chromatography (silica gel, ethyl acetate); yield 67% ethyl [benzyloxycarbonyl-L-leucyl-(2 S)-2-amino-(R,S)-1-hydroxy- 4-methylpentyl](phenyl)phosphinate; MS: 533 m/z (M+H)$^+$; 555 m/z (M+Na) $^+$.

Method E; Ethyl benzyloxycarbonyl-L-leucyl-(2S)-2-amino-(R,S)-1-hydroxy-4-methylpentyl(phenyl) phosphinate; Dess-Martin periodinane; 4 hours; yield 92%; MS: 531 m/z (M+H)$^+$; 553 m/z (M+Na)$^+$.

Example 69

Inhibition and Rate of Inactivation of Cysteine Protease Activity

To evaluate inhibitory activity, stock solutions (40 times concentrated) of each compound to be tested were prepared in 100% anhydrous DMSO and 5 µl of each inhibitor preparation were aliquoted into each of three wells of a 96 well plate. Calpain I, prepared by a modification of the method of W. J. Lee et al. (Biochem. Internatl. 22:163–171 (1990)), was diluted into assay buffer (i.e., 50 mM Tris, 50 mM NaCl, 1 mM EDTA, 1 mM EGTA, and 5 mM β-mercaptoethanol, pH 7.5 including 0.2 mM Succ-Leu-Tyr-MNA) and 175 µl aliquoted into the same wells containing the independent inhibitor stocks as well as to positive control wells containing 5 µl DMSO, but no compound. To start the reaction, 20 µl of 50 mM CaCl$_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor ($v_i$) relative to the rate in its absence ($v_o$). Comparison between $v_o$ and $v_i$ was made within the linear range for substrate hydrolysis. For screening, compounds were tested at 10 µM. Compounds having 50% inhibition at 10 µM were considered active. Apparent second order rate constants were determined from analysis of reaction progress curves under pseudo-first order conditions. Each determination represents the mean of three or more independent single cuvette analyses continually monitored via a Perkin-Elmer LS50B spectrofluorimeter. The rate of inhibition of hydrolysis was obtained by fitting the curve to the exponential equation (1):

$$y=Ae^{-(k_{obs}xt)}+B \quad (1)$$

In the above equation 1, y is $P_t$, which is the amount of product formed at time t; $k_{obs}$ is the pseudo-first order rate constant for inactivation; A is a constant which is the amplitude of the reaction, given by [$P_o-P_\infty$], which is the difference between the product formed at t=0 ($P_o$) and the maximal product formed when the reaction is complete ($P_\infty$); B is a constant which is the maximal product formed when the reaction is complete ($P_\infty$); $k_{app}$ is the apparent second order rate constant, determined as $k_{obs}$/[I], where [I] is inhibitor concentration. $k_{app}$ was corrected for the presence of substrate to give the second order rate constant $k_2$ according to equation (2):

$$k_2=k_{app}(1+[S]/K_m) \quad (2)$$

wherein [S] is substrate concentration, and $K_m$ is the Michaelis constant.

Values for $k_{obs}$/I are given in Table I.

TABLE I

[Structure: X-W-Y-CH(R2)-C(=O)-NH-CH(R1)-C(=O)-[CH(R3)]r-Q]

| Ex. # | X—W—Y— | Q | t | $k_{obs}/I \times 10^{-3}$ $M^{-1}s^{-1}$ | % Inhib. @ 0.1 uM |
|---|---|---|---|---|---|
| | $R_1$ = CH$_2$Ph; $R_2$ = iBu; $R_3$ = H | | | | |
| 34 | C$_6$H$_5$CH$_2$OCONH | OP(O)(OCH$_2$C$_6$H$_5$)$_2$ | 1 | 100 | |
| 35 | t-C$_4$H$_9$OCONH | OP(O)(OCH$_2$C$_6$H$_5$)$_2$ | 1 | 242 | 100 |
| 36 | Morpholinyl sulfonyl-NH | OP(O)(OCH$_2$C$_6$H$_5$)$_2$ | 1 | 182 | |
| 37 | Diisopropylidine-2-keto-L-gulonyl-NH | OP(O)(OCH$_2$C$_6$H$_5$)$_2$ | 1 | 113 | |
| 38 | Monoisopropylidine-2-keto-L-gulonyl-NH | OP(O)(OCH$_2$C$_6$H$_5$)$_2$ | 1 | 116 | |
| 39 | C$_6$H$_5$CH$_2$OCONH | OP(O)(OCH$_2$C$_6$H$_4$-2-CH$_3$)$_2$ | 1 | 365 | |
| 40 | C$_6$H$_5$CH$_2$OCONH | OP(O)(OCH$_2$C$_6$H$_4$-3-OC$_6$H$_5$)$_2$ | 1 | | 53 |
| 41 | t-C$_4$H$_9$OCONH | OP(O)(OH)$_2$ | 1 | <20 | 7 |
| 42 | C$_6$H$_5$CH$_2$OCONH | OP(O)(OCH$_3$)$_2$ | 1 | 20 | |
| 43 | C$_6$H$_5$CH$_2$OCONH | OP(O)(OC$_4$H$_9$)$_2$ | 1 | 40 | |
| 44 | C$_6$H$_5$CH$_2$OCONH | OP(O)(OCH$_2$CH(C$_2$H$_5$)C$_4$H$_9$)$_2$ | 1 | 1 | |
| 45 | t-C$_4$H$_9$OCONH | OP(O)(OCH$_2$CH$_2$—cyclohexyl)$_2$ | 1 | | 28 |
| 46 | C$_6$H$_5$CH$_2$OCONH | OP(O)(OCH$_2$CH$_2$C$_6$H$_5$)$_2$ | 1 | 380 | 99 |
| 47 | C$_6$H$_5$CH$_2$OCONH | OP(O)(OCH$_2$)$_2$CHOCH$_2$C$_6$H$_5$ | 1 | | 47 |
| 48 | C$_6$H$_5$CH$_2$OCONH | OP(O)(CH$_3$)(OCH$_2$C$_6$H$_5$) | 1 | <10 | 0 |
| 49 | C$_6$H$_5$CH$_2$OCONH | OP(O)(C$_6$H$_5$)(OCH$_2$C$_6$H$_5$) | 1 | 337 | 90 |
| 50 | C$_6$H$_5$CH$_2$OCONH | OP(O)(C$_6$H$_5$)(OCH$_2$CH$_2$-morpholine) | 1 | 70 | |
| 51 | C$_6$H$_5$CH$_2$OCONH | OP(O)(C$_6$H$_5$)(OCH$_2$CH$_2$-pyrrolidinone) | 1 | 26 | |
| 52 | C$_6$H$_5$CH$_2$OCONH | OP(O)(CH$_3$)$_2$ | 1 | 6 | |
| 53 | C$_6$H$_5$CH$_2$OCONH | OP(O)(C$_5$H$_{11}$)$_2$ | 1 | | 19 |
| 54 | C$_6$H$_5$CH$_2$OCONH | OP(O)(CH$_2$CH$_2$C$_6$H$_5$)$_2$ | 1 | 8 | 15 |
| 55 | C$_6$H$_5$CH$_2$OCONH | OP(O)(C$_6$H$_4$-2-CH$_3$)$_2$ | 1 | 31 | |
| 56 | t-C$_4$H$_9$OCONH | OP(O)(C$_6$H$_4$-2-CH$_3$)$_2$ | 1 | 22 | |
| 57 | C$_6$H$_5$CH$_2$OCONH | OP(O)(C$_6$H$_4$-4-OCH$_3$)$_2$ | 1 | 85 | 85 |
| 58 | C$_6$H$_5$CH$_2$OCONH | OP(O)(C$_6$H$_5$)(C$_6$H$_4$-2-OCH$_3$) | 1 | 150 | |
| 59 | C$_6$H$_5$CH$_2$OCONH | OP(O)(C$_6$H$_5$)(C$_6$H$_4$-3-OCH$_3$) | 1 | 163 | |
| 60 | C$_6$H$_5$CH$_2$OCONH | OP(O)(C$_6$H$_5$)(C$_2$H$_5$) | 1 | 6 | 51 |
| 61 | C$_6$H$_5$CH$_2$OCONH | OP(O)(C$_6$H$_5$)(CH$_2$—CH$_2$CH$_2$-morpholine) | 1 | 17 | |
| 62 | C$_6$H$_5$CH$_2$OCONH | OP(O)(CH$_2$)$_2$C$_6$H$_4$ | 1 | | 34 |
| 63 | C$_6$H$_5$CH$_2$OCONH | OP(O)(CH$_2$CH=)$_2$ | 1 | | 22 |
| 64 | C$_6$H$_5$CH$_2$OCONH | P(O)(OC$_2$H$_5$)(C$_6$H$_5$) | 1 | 4 | 26 |
| 65 | C$_6$H$_5$CH$_2$OCONH | P(O)(OCH$_3$)(OH) | 0 | | 19 |
| 66 | C$_6$H$_5$CH$_2$OCONH | P(O)(OC$_4$H$_9$)$_2$ | 0 | | 0 |
| 67 | C$_6$H$_5$CH$_2$OCONH | P(O)(OC$_6$H$_5$-4-Cl)$_2$ | 0 | | 4 |
| 68 | C$_6$H$_5$CH$_2$OCONH | P(O)(OC$_2$H$_5$)(C$_6$H$_5$) | 0 | | 0 |

It is intended that each of the patents, publications, and other published documents mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of the formula:

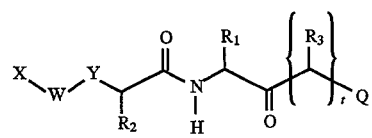

wherein:

X is selected from the group consisting of aryl having from about 6 to about 14 carbons, heteroaryl having from about 6 to about 14 ring atoms, aralkyl having from about 7 to about 15 carbons, alkyl having from 1 to about 10 carbons, said alkyl groups being optionally substituted with one or more J groups, heteroalkyl having from 2 to about 7 carbons, alkoxy having from 1 to about 10 carbons, aralkyloxy having from about 7 to about 15 carbons, and a carbohydrate moiety optionally containing one or more alkylated hydroxyl groups;

W is selected from the group consisting of carbonyl and $SO_2$;

Y is selected from the group consisting of NH and $(CH_2)_k$ where k is an integer from 0 to 3;

$R_1$ and $R_2$ are independently selected from the group consisting of hydrogen, alkyl having from one to about 14 carbons, and cycloalkyl having from 3 to about 10 carbons, said alkyl and cycloalkyl groups being optionally substituted with one or more J groups;

$R_3$ is selected from the group consisting of hydrogen, lower alkyl, aryl, heteroaryl, aralkyl, and heteroaralkyl;

t is 0 or 1;

J is selected from the group consisting of halogen, alkyl, aryl, heteroaryl, amino optionally substituted with one to three aryl or lower alkyl groups, guanidino, alkoxycarbonyl, alkoxy, hydroxy, aryloxy, aralkyloxy, heteroalkyl, and carboxy; and Q has the formula

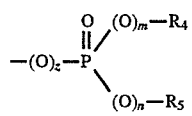

wherein:

m, n, and z are each independently 0 or 1;

$R_4$ and $R_5$ are each independently selected from the group consisting of hydrogen, lower alkyl optionally substituted with J, aryl optionally substituted with J, aralkyl optionally substituted with J, and heteroaryl optionally substituted with J;

or $R_4$ and $R_5$ may be taken together along with the —$(O)_m$—P(=O)—$(O)_n$— of Q to form a 5–8 membered heterocyclic ring optionally substituted with J;

or $R_4$ and $R_5$ may be taken together to form an aralkyl group;

with the proviso that when t is 0, z is also 0; and with the proviso that when m and n are both 0, and t and z are both 1, $R_4$ and $R_5$ cannot be unsubstituted phenyl or halogen-substituted phenyl; and with the further proviso that when $R_1$ is alkylene substituted with J, then J cannot be carboxy or alkoxycarbonyl.

2. A compound of claim 1 wherein z is 0.

3. A compound of claim 1 wherein z is 1.

4. A compound of claim 1 wherein both m and n are 1.

5. A compound of claim 4 wherein $R_4$ and $R_5$ are independently selected from the group consisting of hydrogen, lower alkyl optionally substituted with J, aryl substituted with J, and aralkyl optionally substituted with J; or $R_4$ and $R_5$ taken together along with the —$(O)_m$—P(=O)—$(O)_n$— of Q form a six membered ring that is substituted by J.

6. A compound of claim 5 wherein J is independently selected from the group consisting of alkyl, aryl, aryloxy, and halogen.

7. A compound of claim 6 wherein $R_4$ and $R_5$ are independently selected from the group consisting of hydrogen, lower alkyl, lower alkyl substituted with alkyl, lower alkyl substituted with aryl, aryl substituted with halogen, aralkyl, aralkyl substituted with alkyl, and aralkyl substituted with aryloxy, or $R_4$ and $R_5$ taken together along with the —$(O)_m$—P(=O)—$(O)_n$— of Q form a six membered ring that is substituted by aralkyloxy.

8. A compound of claim 7 wherein $R_4$ and $R_5$ are independently selected from the group consisting of H, methyl, butyl, 2-ethylhexyl, 2-cyclohexylethyl, 2-phenylethyl, 4-chlorophenyl, benzyl, 2-methylbenzyl, and 3-phenoxybenzyl, or $R_4$ and $R_5$ taken together along with the —$(O)_m$—P(=O)—$(O)_n$— of Q form a six-membered ring having the formula:

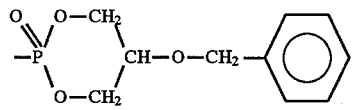

9. A compound of claim 8 wherein $R_4$ and $R_5$ are independently selected from the group consisting of benzyl, 2-methylbenzyl, and 2-phenylethyl.

10. A compound of claim 1 wherein m and n are 0.

11. A compound of claim 10 wherein $R_4$ and $R_5$ are independently selected from the group consisting of lower alkyl optionally substituted with J, aralkyl, and aryl optionally substituted with J, or $R_4$ and $R_5$, taken together along with the —$(O)_m$—P(=O)—$(O)_n$— of Q form a five membered ring.

12. A compound of claim 11 wherein J is independently selected from the group consisting of alkyl, aryl, heteroalkyl, and alkoxy.

13. A compound of claim 12 wherein $R_4$ and $R_5$ are independently selected from the group consisting of lower alkyl optionally substituted with alkyl or aryl, lower alkyl substituted with heteroalkyl, aryl optionally substituted with alkyl or alkoxy, or $R_4$ and $R_5$, taken together along with the —$(O)_m$—P(=O)—$(O)_n$— of Q form a five membered ring.

14. A compound of claim 13 wherein $R_4$ and $R_5$ are independently selected from the group consisting of methyl, ethyl, pentyl, 2-phenylethyl, phenyl, 2-methylphenyl, 2-methoxyphenyl, 3-methoxyphenyl, 4-methoxyphenyl, and 3-morpholinopropyl, or $R_4$ and $R_5$, taken together along with the —$(O)_m$—P(=O)—$(O)_n$— of Q to form a five-membered ring having the formula:

or the formula

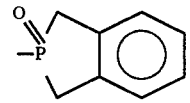

15. A compound of claim 1 wherein m is 1 and n is 0.

16. A compound of claim 15 wherein $R_4$ and $R_5$ are independently selected from the group consisting of lower alkyl optionally substituted with J, aryl, and aralkyl.

17. A compound of claim 16 wherein J is heteroalkyl.

18. A compound of claim 17 wherein $R_4$ and $R_5$ are independently selected from the group consisting of methyl, ethyl, benzyl, phenyl, 2-morpholinoethyl, and 2-(2-oxopyrrolidin-1-yl)ethyl.

19. A compound of claim 1 wherein t is 1.
20. A compound of claim 1 wherein t is 0.
21. A compound of claim 1 having the formula:

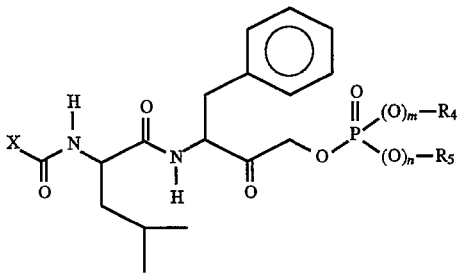

22. A compound of claim 21 wherein X is selected from the group consisting of alkoxy having from 1 to about 10 carbons, aralkyloxy having from about 7 to about 15 carbons, and a carbohydrate moiety optionally containing one or more alkylated hydroxyl groups.
23. A compound of claim 22 wherein X is selected form the group consisting of benzyloxy, t-butoxy, diisopropylidine-2-keto-L-gulonyl, and monoisopropylidine-2-keto-L-gulonyl.
24. A compound of claim 21 wherein m and n are 1.
25. A compound of claim 24 wherein $R_4$ and $R_5$ are independently selected from the group consisting of hydrogen, lower alkyl optionally substituted with J, aryl substituted with J, and aralkyl optionally substituted with J; or $R_4$ and $R_5$ taken together along with the $-(O)_m-P(=O)-(O)_n-$ of Q form a six membered ring that is substituted by J.
26. A compound of claim 25 wherein J is independently selected from the group consisting of alkyl, aryl, aryloxy, and halogen.
27. A compound of claim 26 wherein $R_4$ and $R_5$ are independently selected from the group consisting of hydrogen, lower alkyl, lower alkyl substituted with alkyl, lower alkyl substituted with aryl, aryl substituted with halogen, aralkyl, aralkyl substituted with alkyl, and aralkyl substituted with aryloxy, or $R_4$ and $R_5$ taken together along with the $-(O)_m-P(=O)-(O)_n-$ of Q form a six membered ring that is substituted by aralkyloxy.
28. A compound of claim 27 wherein $R_4$ and $R_5$ are independently selected from the group consisting of H, methyl, butyl, 2-ethylhexyl, 2-cyclohexylethyl, 2-phenylethyl, 4-chlorophenyl, benzyl, 2-methylbenzyl, and 3-phenoxybenzyl, or $R_4$ and $R_5$ taken together along with the $-(O)_m-P(=O)-(O)_n-$ of Q form a six-membered ring having the formula:

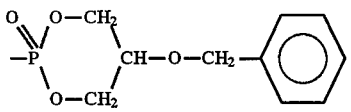

29. A compound of claim 28 wherein $R_4$ and $R_5$ are lo independently selected from the group consisting of benzyl, 2-methylbenzyl, and 2-phenylethyl.
30. A compound of claim 21 wherein m and n are 0.
31. A compound of claim 30 wherein $R_4$ and $R_5$ are independently selected from the group consisting of lower alkyl optionally substituted with J, aralkyl, and aryl optionally substituted with J, or $R_4$ and $R_5$, taken together along with the $-(O)_m-P(=O)-(O)_n-$ of Q form a five membered ring.
32. A compound of claim 31 wherein J is independently selected from the group consisting of alkyl, aryl, heteroalkyl, and alkoxy.

33. A compound of claim 32 wherein $R_4$ and $R_5$ are independently selected from the group consisting of lower alkyl optionally substituted with alkyl or aryl, lower alkyl substituted with heteroalkyl, aryl optionally substituted with alkyl or alkoxy, or $R_4$ and $R_5$, taken together along with the $-(O)_m-P(=O)-(O)_n-$ of Q form a five membered ring.
34. A compound of claim 33 wherein $R_4$ and $R_5$ are independently selected from the group consisting of methyl, ethyl, pentyl, 2-phenylethyl, phenyl, 2-methylphenyl, 2-methoxyphenyl, 3-methoxyphenyl, 4-methoxyphenyl, and 3-morpholinopropyl, or $R_4$ and $R_5$, are taken together along with the $-(O)_m-P(=O)-(O)_n-$ of Q to form a five-membered ring having the formula:

or the formula

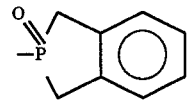

35. A compound of claim 21 wherein m is 1 and n is 0.
36. A compound of claim 35 wherein $R_4$ and $R_5$ are independently selected from the group consisting of lower alkyl optionally substituted with J, aryl, and aralkyl.
37. A compound of claim 36 wherein J is heteroalkyl.
38. A compound of claim 37 wherein $R_4$ and $R_5$ are independently selected from the group consisting of methyl, ethyl, benzyl, phenyl, 2-morpholinoethyl, and 2-(2-oxopyrrolidin-1-yl)ethyl.
39. A compound of claim 1 wherein t is 1; z is 1; J is selected from the group consisting of halogen, lower alkyl, aryl, heteroaryl, amino optionally substituted with one to three aryl or lower alkyl groups, guanidino, alkoxycarbonyl, alkoxy, hydroxy, and carboxy; and $R_4$ and $R_5$ are each independently selected from the group consisting of hydrogen, lower alkyl optionally substituted with J, aryl optionally substituted with J, heteroaryl optionally substituted with J; or $R_4$ and $R_5$ may be taken together along with the $-(O)_m-P(=O)-(O)_n-$ of Q to form a 5–8 membered heterocyclic ring; or $R_4$ and $R_5$ may be taken together to form a 5–8 membered ring optionally substituted with J.
40. A compound of claim 1 wherein X is benzyloxy; W is carbonyl; Y is NH; $R_1$ is benzyl; $R_2$ is isobutyl; $R_3$ is hydrogen; t, z, m, and n are each 1; and $R_4$ and $R_5$ are each 2-methylbenzyl.
41. A compound of claim 1 wherein X is benzyloxy; W is carbonyl; Y is NH; $R_1$ is benzyl; $R_2$ is isobutyl; $R_3$ is hydrogen; t, z, m, and n are each 1; and $R_4$ and $R_5$ are each 2-phenylethyl.
42. A compound of claim 1 wherein X is benzyloxy; W is carbonyl; Y is NH; $R_1$ is benzyl; $R_2$ is isobutyl; $R_3$ is hydrogen; t, z, are each 1; m is 1; n is 0; $R_4$ is benzyl; and $R_5$ is phenyl.
43. A composition for inhibiting a protease selected from the group consisting of serine proteases and cysteine proteases comprising a compound of claim 1.
44. A method for inhibiting a protease comprising contacting a protease selected from the group consisting of serine proteases and cysteine proteases with an inhibitory amount of a compound of claim 1.

* * * * *

UNITED STATES PATENT AND TRADEMARK OFFICE
CERTIFICATE OF CORRECTION

PATENT NO. : 5,639,732
DATED : Jun. 17, 1997
INVENTOR(S) : Mallamo et al.

It is certified that error appears in the above-identified patent and that said Letters Patent is hereby corrected as shown below:

On the title page, under "References Cited", "OTHER PUBLICATIONS" section, second column, at "Schlemmer", line 4 thereof, please delete "registricy" and insert --registry-- therefor.

In column 2, line 1, please delete "vital" and inset --viral-- therefor.

In column 4, line 36, at the beginning of the line, please delete "j" and insert --J-- therefor.

In column 6, line 21, at the beginning of the line, please delete the first occurrence of "halogen" and insert --atoms. The-- therefor.

In column 10, line 66, please delete "given for of" and insert --given for-- therefor.

In column 11, line 19, please delete "(2benzyloxy) and insert --(2-benzyloxy)-- therefor.

In column 11, line 50, please delete "retool)" and insert --mmol)-- therefor.

In column 14, line 59, please delete "retool)" and insert --mmol)-- therefor.

UNITED STATES PATENT AND TRADEMARK OFFICE
CERTIFICATE OF CORRECTION

PATENT NO. : 5,639,732
DATED : Jun. 17, 1997
INVENTOR(S) : Mallamo et al.

It is certified that error appears in the above-identified patent and that said Letters Patent is hereby corrected as shown below:

In column 14, line 62, please delete "(15" and insert --(15 ml)-- therefor.

In column 15, line 8, please delete (678g," and insert --6.8 g,-- therefor.

In column 16, line 26, please delete "29 From" and insert --29. From-- therefor.

In column 17, line 22, please delete "retool)" and insert --mmol)-- therefor.

In column 18, line 8, at the end of the line, after "(M+H);", please insert --831 m/z (M+Na).--

In column 18, line 17, please delete "(0,015" and insert --(0.015-- therefor.

In column 19, line 52, please delete "dioxaphosphosrinane" and insert --dioxaphosphorinane-- therefor.

In column 20, line 28, please delete "4phenylbutyl]" and insert --4-phenylbutyl]-- therefor.

In column 20, line 49, please delete "4phenylbutyl]" and insert --4-phenylbutyl]-- therefor.

UNITED STATES PATENT AND TRADEMARK OFFICE
CERTIFICATE OF CORRECTION

PATENT NO. : 5,639,732
DATED : Jun. 17, 1997
INVENTOR(S) : Mallamo et al.

It is certified that error appears in the above-identified patent and that said Letters Patent is hereby corrected as shown below:

In column 20, line 58, please delete "4phenylbutyl]" and insert --4-phenylbutyl]-- therefor.

In column 21, line 2, please delete "4phenylbutyl]" and insert --4-phenylbutyl]-- therefor.

In column 21, line 12, please delete "4phenylbutyl]" and insert --4-phenylbutyl]-- therefor.

In column 21, line 21, please delete "4phenylbutyl]" and insert --4-phenylbutyl]-- therefor.

In column 21, line 43, please delete "(3-methoxylphenyl)" and insert --3-methoxyphenyl)-- therefor.

In column 21, line 45, please delete "(3-methoxylphenyl)" and insert --3-methoxyphenyl)-- therefor.

In column 21, line 56, please delete "$C_{32}H_{39}N_2O_7P:C,$" and insert --$C_{32}H_{39}N_2O_6P:C,$-- therefor.

In column 22, line 21, please delete "oxo-4phenylbutyl]" and insert --oxo-4-phenylbutyl]-- therefor.

UNITED STATES PATENT AND TRADEMARK OFFICE
CERTIFICATE OF CORRECTION

PATENT NO. : 5,639,732
DATED : Jun. 17, 1997
INVENTOR(S) : Mallamo et al.

It is certified that error appears in the above-identified patent and that said Letters Patent is hereby corrected as shown below:

In column 23, line 14, please delete "methylpentyl)bis(4chlorophenyl)phosphine" and insert --methylpentyl)bis(4-chlorophenyl)phosphine-- therefor.

In column 29, claim 29, line 55, at the end of the line, please delete "lo".

Signed and Sealed this

Thirtieth Day of December, 1997

Attest:

BRUCE LEHMAN

Attesting Officer

Commissioner of Patents and Trademarks